United States Patent [19]
Apter et al.

[11] Patent Number: 5,136,157
[45] Date of Patent: Aug. 4, 1992

[54] APPARATUS FOR THE THREE-DIMENSIONAL INSPECTION OF HOLLOW BODIES WITH PLURAL MIRROR FOR GENERATING PLURAL PARTIAL IMAGES

[75] Inventors: Robert Apter, Dübendorf, Switzerland; Louis-François Pau, Chemin d'Aubagne, France; Carsten Agerskov, Killwangen, Switzerland; Ulrik Jacobi, Hellerup; Henrik Sloth, Vanlose, both of Denmark

[73] Assignee: Elpatronic AG, Zug, Switzerland

[21] Appl. No.: 617,572

[22] Filed: Nov. 26, 1990

[30] Foreign Application Priority Data

Dec. 19, 1989 [CH] Switzerland ............... 04 560/89
Jun. 15, 1990 [CH] Switzerland ............... 02 006/90

[51] Int. Cl.⁵ .............................................. G06M 7/00
[52] U.S. Cl. ........................... 250/223 B; 356/240
[58] Field of Search ............ 250/223 B, 222.1; 356/239, 240

[56] References Cited

U.S. PATENT DOCUMENTS 3,942,001 3/1976 O'Connor ............... 250/223 B
4,620,090 10/1986 Ducloux ............... 356/240
4,636,635 1/1987 Krönseder ............... 250/223 B
4,855,608 8/1989 Peterson, II ............... 250/222.1

FOREIGN PATENT DOCUMENTS 0151059 8/1985 European Pat. Off. .
0293510 12/1988 European Pat. Off. .

Primary Examiner—David C. Nelms
Assistant Examiner—Que T. Le
Attorney, Agent, or Firm—McCormick, Paulding & Huber

[57] ABSTRACT

A conveyor (12) moves the hollow bodies (18) over a circular path through an inspection region (20) in which the hollow bodies (18) are homogeneously illuminated by an illumination device (16). The light issuing from the hollow bodies (18) passes via a group (34) of four mirrors (34a–34d) and a deflecting mirror (36) to a matrix camera or line scanning camera (30). The mirrors (34a–32d) are plane mirrors which are inclined at an angle in relation to one another. The hollow bodies (18) execute one complete revolution about their longitudinal axis while passing through the inspection region (20). Therefore, the group (34) of four mirrors views a quarter of the circumference of the hollow bodies each time in succession. The inspection apparatus is particularly suitable for inspecting the threaded region of bottles and has the advantage that is does not need any moving parts.

11 Claims, 5 Drawing Sheets

APPARATUS FOR THE THREE-DIMENSIONAL INSPECTION OF HOLLOW BODIES WITH PLURAL MIRROR FOR GENERATING PLURAL PARTIAL IMAGES

BACKGROUND OF THE INVENTION

The invention relates to an apparatus for the three-dimensional inspection of hollow bodies;

having a conveyor for moving the hollow bodies through an inspection region over a circular path with simultaneous rotation of the hollow bodies about an axis of symmetry which is parallel to the axis of the circular path, having an illuminating device for the hollow bodies which are in the inspection region, having a photoelectric-detector to receive the light which issues from the hollow bodies which are in the inspection region, and having a group of fixed, plane mirrors which are arranged in the path of light and at an angle to one another.

A apparatus of the above-mentioned kind known from EP-B1-0 151 059 serves for the inspection of the whole surface of translucent hollow bodies. The known apparatus has a continuously moved conveying star wheel as a conveyor, with which there is associated an external member for rotating the hollow bodies about their axis of symmetry. The illuminating device consists of a laser light source which directs a laser beam via a rotating mirror with a horizontal axis onto a group of four fixed, plane mirrors which are arranged one above the other in a vertical row. Because of the rotation of the rotating mirror, the plane mirrors deliver a vibrating beam of light which is thrown onto the hollow bodies via a vibrating mirror. The vibrating mirror accompanies the hollow bodies rotating in front of it, by its vibrating movement during a complete revolution and in the course of this sweeps over the hollow bodies with the beam of light in successive diametral planes. The photodetector is a receiver with a light-sensitive screen which is illuminated by the light shining through. In the known apparatus, a driving belt serves as a member for rotating the articles, which belt rests on the side of the hollow bodies adjacent to the light-sensitive screen, at their side wall, at an intermediate height and shades the hollow bodies in this region as a result. In order that this region situated in the blind angle may also be able to be inspected, the vertical row of fixed mirrors is provided, which deliver converging beams of light at different angles of inclination so that the whole surface of the hollow body can be inspected in the light shining through, circumventing the driving belt.

It is a disadvantage in the known apparatus that it needs moving mirrors, namely one rotating mirror and one vibrating mirror, the movement of which must be adapted precisely to one another and to the movement of the star wheel and must remain so adapted. This becomes particularly difficult if a line scanning camera or the like is used as a photodetector, the processor of which has to combine the individual lines at the right time to form a complete picture of the hollow body to be inspected. What is also problematical is that a moving mirror such as the vibrating mirror, which, in the known apparatus, is entrained by a mechanical cam in the direction of movement of the conveyor over the inspection region and is then rapidly returned, is subject to wear and at least require constant re-adjustment. In the known apparatus, however, the vibrating mirror cannot be dispensed with because otherwise no adequate inspection time would be available. There is no information in EP-B1-0 151 059 about the method of evaluating the pictures delivered by the light-sensitive screen of the known apparatus.

An apparatus which is provided for the inspection of the side walls of bottle is known from EP-A2-0 293 510. In this known apparatus, use is likewise made of a vibrating mirror and even of a vibrating lens in order to follow the bottle to be inspected from the beginning to the end of the inspection region. This known apparatus therefore has the same disadvantages as the known apparatus first mentioned above. In addition to this, the problems must be even greater when using a vibrating lens instead of a vibrating mirror, because the optical system must be moved extremely accurately if usable pictures are to be achieved at all.

SUMMARY OF THE INVENTION

It is the object of the invention to develop an apparatus of the kind mentioned at the beginning so that no moving mirrors are necessary.

The device for achieving the object has an illuminating system which illuminates the hollow bodies homogeneously within the inspection region. Its photoelectric transducer is part of a matrix or line-scanning camera with an associated processor and monitor for image processing. Furthermore, it has a group of n fixed, planar mirrors arranged between the inspection region and the matrix or line-scanning camera. These mirrors are aligned angularly offset in such a way that they simultaneously cover the entire inspection region and that they direct the light emerging from n mutually contiguous segments of the inspection region via in each case one of the n mirrors onto the photoelectric transducer in a manner so offset that said transducer simultaneously receives in each case n partial images—one each from each segment—in sequence.

In this solution, the only parts of the device that are moved are the conveyor and the hollow bodies, which are moved by the latter on a circular path and are thereby rotated about their axis of symmetry. In the case in which a source of transmitted light is employed as an illuminating system, said hollow bodies are preferably transparent bottles having a closure thread that is to be inspected in order to detect defects. In the case in which a source of reflected light is employed as illuminating system, the hollow bodies are preferably light-proof or opaque (e.g. tins).

The homogeneous illumination of the hollow bodies inside the inspection region can be achieved, for example, when, starting from a point light source, a funnel-shaped light beam is produced via a diverging lens and a slotted diaphragm. However, it is also possible to employ an illuminating system which comprises distributed light sources and a diffusely transparent plate.

The ratio of the rotational speed of the hollow bodies (angular velocity with which the hollow bodies rotate) is (in the case of n fixed mirrors in the device) selected with reference to the rotational speed of conveyance (angular velocity with which the conveyor rotates) in such a way that inside the inspection region each hollow body executes a complete revolution about its axis of symmetry and an 1/n revolution before each mirror. In this process the mutual angular separation between two sequential hollow bodies transported on the conveyor is 2/n of that angle subtended by the circular path through which the conveyor passes within the inspection region. By appropriately selecting the directions of rotation, the rotation of the hollow bodies about the axis of symmetry and the rotary movement of the conveyor can be added to one another.

The fixed mirrors can be arranged offset in height behind one another and can be angled with respected to the vertical and to one another in such a way that it is possible sequentially with each mirror for the same vertical region of the hollow body to be imaged on the photoelectric transducer, and that the regions arranged behind one another over the circular path are imaged on the monitor in a juxtaposed sequence with the aid of the mirrors and the image-processing processor (possibly after temporary storage). The angular setting of all the mirrors is adjustable, and a deflecting mirror can be arranged in the light beam path between the group of fixed mirrors and the photoelectric transducer.

BRIEF DESCRIPTION OF THE DRAWINGS

Examples of embodiment of the invention are described in more detail below with reference to the drawings.

DESCRIPTION OF THE PREFERRED EMBODIMENTS

The invention is described below with reference to the example of the inspection of transparent bottles 18 (FIGS. 1 to 5) and of less transparent or non-transparent bottles (FIG. 6), and using a group of four mirrors, the apparatus being intended to be used for the inspection of the mouth region of the bottles, provided with a screw thread. Instead of this, the apparatus could also be used for the inspection of other regions of bottles or other more or less transparent bodies of all kinds, such as hollow glassware, hollow bodies of PET, tin cans etc.

Figure 1:
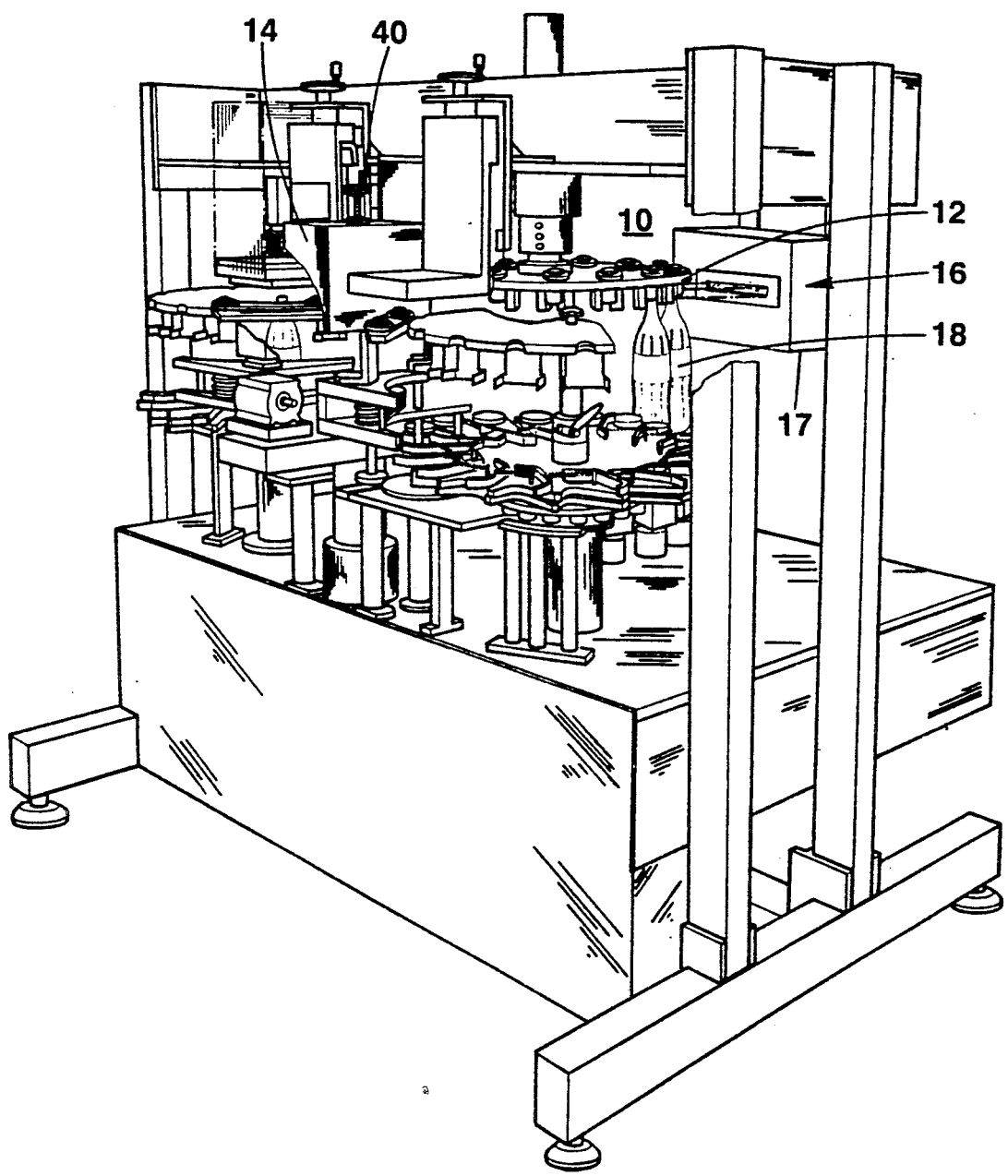
FIG. 1 shows a general view in perspective of a bottle inspecting machine which is provided with a first form of embodiment of the inspection device according to the invention.

FIG. 1 shows a general view of a bottle inspection machine which comprises an inspection device designated as a whole by 10 for the mouth region of the bottles provided with a thread. Provided behind the two rotary tables illustrated at the front in FIG. 1 is a third rotary table 12 which is associated with the inspection device 10. The inspection device 10 consists of an inspection unit 14 and an illumination device 16 with a housing 17 (which has been omitted in FIGS. 2 and 4 for the sake of clarity).

Figure 2:
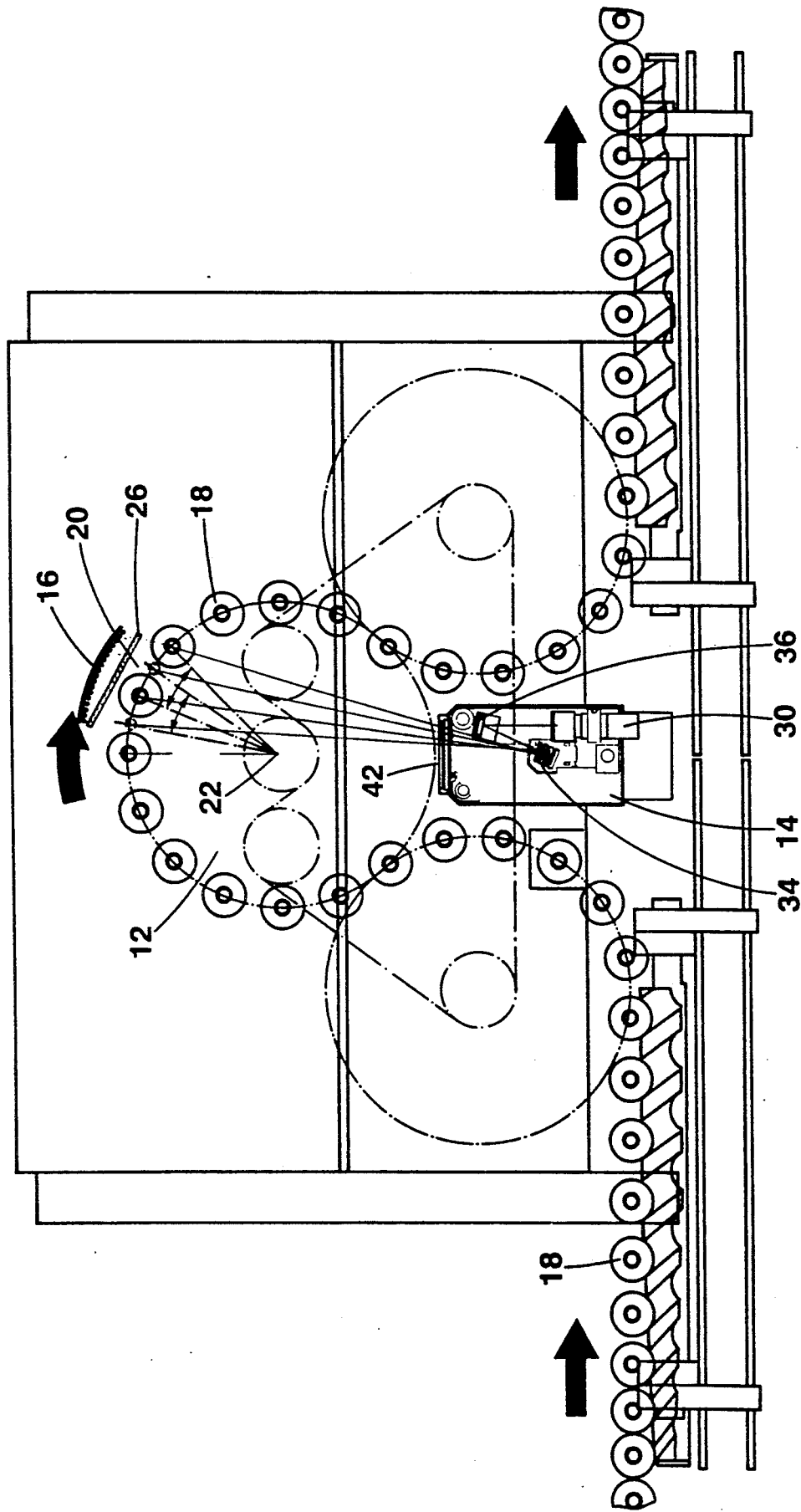
FIG. 2 shows the inspection plane of the bottle inspecting machine according to FIG. 1, in plan view.

According to FIG. 2, bottles 18 to be inspected are feed by means of a worm screw spindle to the front rotary table illustrated on the left which delivers the bottles 18 to the third rotary table 12 which is constructed in the form of a turntable and which in turn delivers the bottle 18, after the inspection, to the front rotary table which is illustrated on the right and from which they are removed by a further worm screw spindle. The conveying direction is indicated by black arrows in each case in FIG. 2. The rotary table 12 moves the bottles 18 over a circular path through an inspection region 20. In the course of this, the bottles 18 are rotated about their axis of symmetry, that is to say about their longitudinal axis which is parallel to the axis 22 of the circular path, that is to say to the centre axis of the rotary table 12. A driving belt 24, which is illustrated only in FIG. 3, serves to rotate the bottles 18 about their longitudinal axis.

In the example of embodiment illustrated in FIGS. 1 to 5, the illumination device 16, which is arranged outside the circular path at the side thereof remote from the inspection unit 14, comprises the housing 17 which has a slit at the front which is covered with a plate 26 of heat-resistant glass. The plate 26 is sand-blasted so that it is diffusely transparent and it receives light from a scattered light source 28. The illumination device 16 thus effects a homogeneous illumination of the bottles 18 in the whole inspection region 20.

According to the illustration in FIGS. 2 to 5, the inspection unit 14 includes a scanning camera 30 and a group 34 of fixed, plane mirrors 34a-34d which are arranged in the path of light rays 32 between the inspection region 20 and a photoelectric transducer, not illustrated, of the camera. The mirrors 34a-34d are arranged in a horizontal row extending transversely to the axis 22 of the circular path and are offset laterally in relation to one another, that is to say they form an angle W (FIG. 3) with one another in the horizontal plane. The unillustrated photoelectric transducer of the camera is for example a linear CCD detector. A deflecting mirror 36 is provided between the group 34 of mirrors and the camera 30 in the inspection unit 14. The camera 30, the mirror 36 and the group 34 of mirrors are jointly secured to a plate 38 which is adjustable in height by means of a handwheel 40 in a manner which can be seen in FIG. 5. The inspection device 14 has, at the entry side of the path of light rays 32, a window with an admission pane 42, the height of which is adapted to the range of adjustment in height of the plane 38. The inspection unit 14 is secured to the frame of the bottle inspecting machine by means of a bracket 44.

Figure 3:
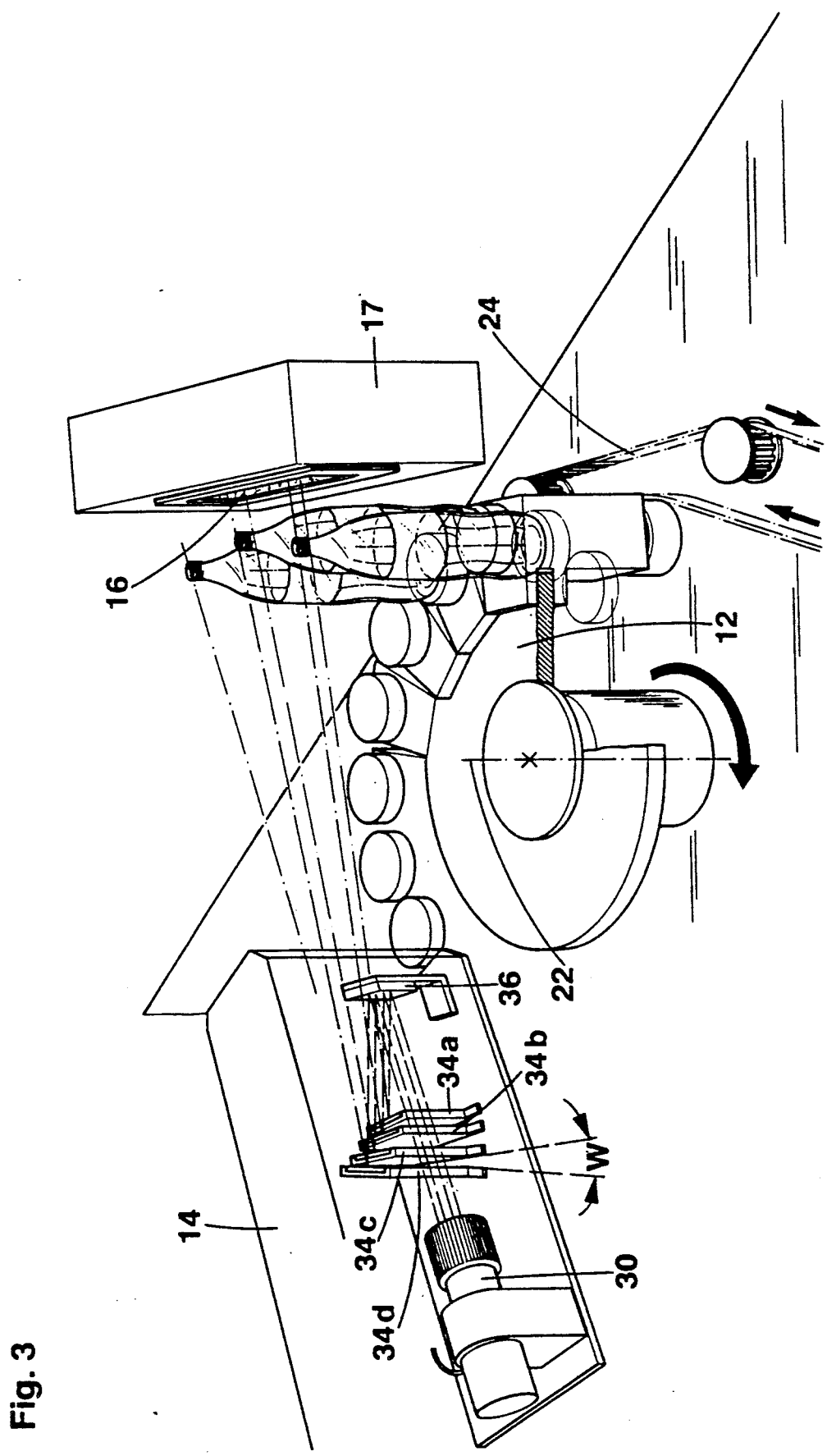
FIG. 3 shows, as a detail, illustrated in perspective, the inspection device according to FIG. 1.
Figure 5:
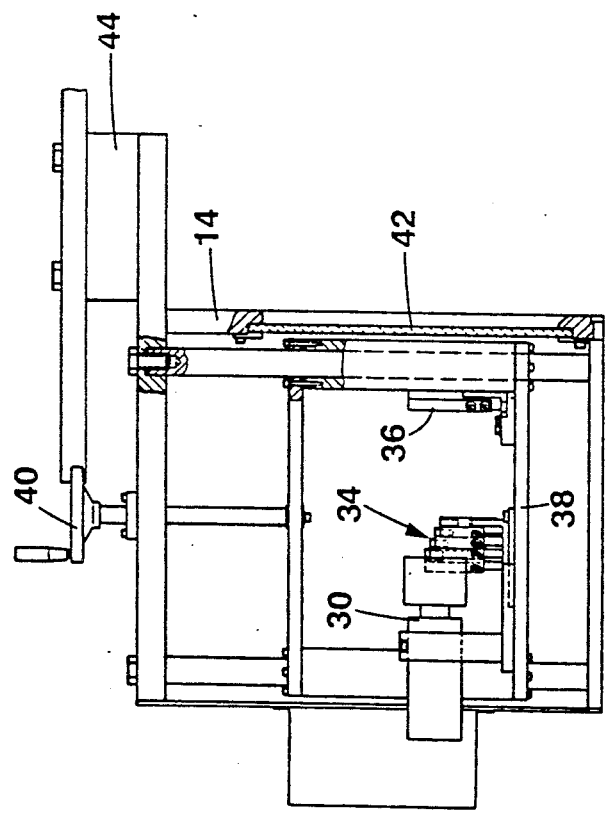
FIG. 5 shows a view of the camera with associated mirrors in the direction of an arrow V in FIG. 4.
Figure 4:
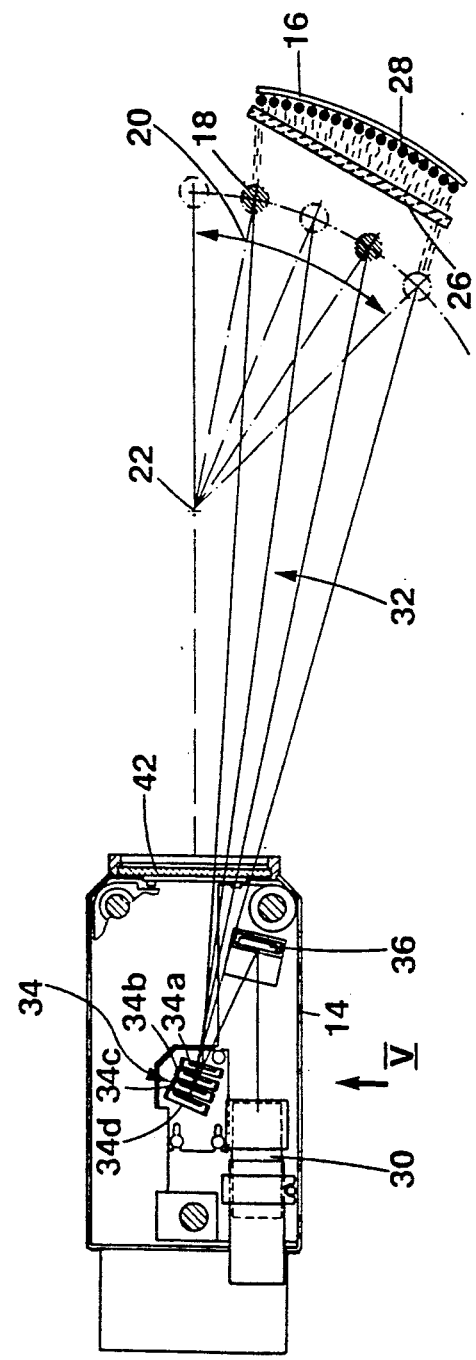
FIG. 4 shows as a detail in plan view, the inspection device according to FIG. 1.

From the illustration in FIGS. 3 and 5, it can further be seen that the mirrors 34a-34d are arranged one behind the other, staggered in height. In addition, the mirrors 34a-34d are inclined at an angle to the vertical so that the same vertical region of the bottle 18 is imaged by each mirror on the photoelectric transducer for the inspection. The thread regions of the bottles 18, which regions are to be inspected in succession over the circular path, are reproduced one above the other in lines by the mirrors 34a-34d on the line scanning camera 30, as can be seen from the illustration in FIGS. 2 to 4. The mirrors 34a-34d are positioned in a way that is not shown in detail, so that each time their mutual angle W can be adjusted and set.

Once the adjustment has been carried out, the four beams of light of the path of light rays 32, which go from the bottles 18 in the inspection region to the four mirrors 34a-34d and from these to the line scanning camera 30, are fixed. At a particular moment $t_1$, two bottles are in the hatched position in FIG. 4 and are therefore seen by the mirror 34a and the mirror 34c. The mirrors 34b and 34d do not see any bottles 18 at the moment $t_1$ because these are not opposite any bottles at this moment. At a moment $t_2$, when the bottles have travelled onwards the mirrors 34b and 34d each see a bottle 18 and, the mirrors 34a and 34c do not see any bottles. Thus the mirrors 34a, 34c or 34b, 34d always see a bottle 18, since two mirrors are directed towards the centre of the spacing (hatched positions) and two mirrors towards the spacing positions (unhatched positions). Because each bottle 18 rotates about its longitudinal axis simultaneously with its translatory movement along the circular path, and executes one complete revolution about its longitudinal axis within the inspection region 20, each mirror 34a–34d views a quarter of the circumference of the bottle, in its thread region. Two quarters of two different bottles are received simultaneously each time because two mirrors see two bottles at the time $t_1$ and the other two mirrors see two bottles at the time $t_2$.

Associated with the camera 30 is a processor, not illustrated, which is a single-image store with associated line scan interface so that the line detector images which the photodetector delivers can be combined line by line in order to produce a development of the three-dimensional thread image in two dimensions. A digital storage device ensures that the detector output signals are recorded at all times and are then represented in the correct position and mutual relationship. A monitor following the line scanning camera 30 then displays the four images one above the other, the display line consisting of four parts which have been received by the four mirrors in succession. The image received by the first mirror 34a forms the lowest quarter of the line and the other quarter images are arranged above it as can be seen from FIG. 3.

The example of embodiment described above relates to n=4 mirrors. In order that an image of the whole circumference of each bottle moving through the inspection region 20 may be formed, the ratio of the speed of rotation of the bottles about their own longitudinal axis to the speed of the conveyor 12 must be selected so that each bottle executes 1/n revolution in front of each mirror in the inspection region 20.

The directions of the rotation of the bottles about the longitudinal axis of the bottles and of the movement of the conveyor 12 are selected, for example, so that the speed of rotation of the bottles and the conveyor rotational speed are added in the inspection region 20. If therefore, for example in accordance with the illustration in FIG. 3, the conveyor 12 rotates in clockwise direction, the bottles 18 must be set in rotation in the inspection region by the driving belt 24 (the direction of movement of which is indicated by arrows) so that they rotate about their longitudinal axis in counter-clockwise direction. Seen from the group of mirrors 34, therefore, a point on the bottle moves towards the right in the inspection region as a result of the movement of translation of the conveyor 12. The bottle's own rotational movement about its longitudinal axis, which has the same direction in the inspection region as seen from the group of mirrors, is superimposed on this movement, that is to say it is added to the conveyor speed.

Furthermore, in the example of embodiment described above, a line scanning camera 30 was used for purposes of explanation. A matrix camera could, of course, equally well be used. It is merely a question of the line-scan frequency or single-image frequency. The matrix cameras available today are considerably slower than line scanning cameras. If a matrix camera with a sufficiently high single-image frequency is available, such a camera can easily be used instead of the line scanning camera. In this case, however, it must be borne in mind that with a sufficiently high single-image frequency of a matrix camera, this must also have a sufficiently large detector matrix, that is to say a sufficiently large number of pixels. With a 64×64 detector matrix and a single-image frequency of 2000 single images per section, which is sufficient in itself, too little resolution would result if a bottle having a height of 35 or 40 centimeters had to be scanned with such a matrix camera.

Figure 6:
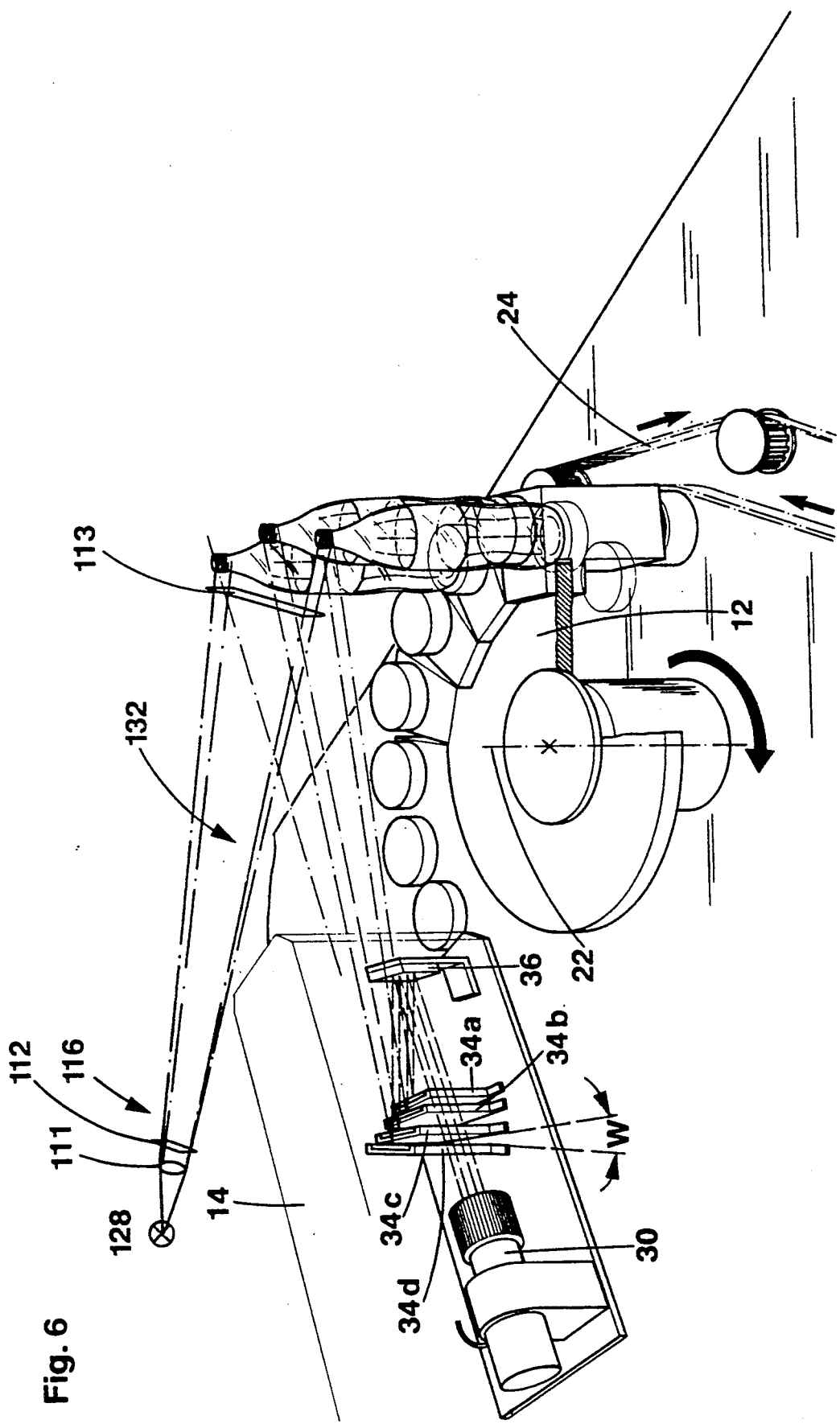
FIG. 6 shows, in a view as in FIG. 3, a second form of embodiment of the inspection device according to the invention.

The mirror arrangement as shown in the example of embodiment according to FIGS. 1 to 5 can be used unaltered if a front or incident-illumination device according to FIG. 6 is used instead of a transmission illumination device as in the form of embodiment according to FIGS. 1 to 5. This second form of embodiment of the inspection apparatus according to the invention can also be used to inspect translucent or transparent hollow bodies although the transmission-illumination device previously described is better suited to the latter. The form of embodiment according to FIG. 6 is more likely to be used for the inspection of bottles 18 of opaque plastics material or sheet metal or of tin cans or the like.

In the form of embodiment according to FIG. 6, the illumination device designated as a whole by 116 has a point light source 128 which is arranged above the mirrors 34a–34d and illuminates the bottles in the inspection region with a fan-shaped beam 132 through a dispersive lens 111 and a slit diaphragm 112 arranged close in front of this as well as through a further slit diaphragm 113 arranged close in front of the bottles 18. A housing, which has not been illustrated in FIG. 6 for the sake of clarity, is usually provided to hold the point light source 128, the dispersive lens 111 and the slit diaphragms 112, 113. The images which the mirrors 34a–34d receive from the bottles 18 are further processed in the manner described with reference to the first example of embodiment. The only difference is that here these images have been produced by reflection of incident light whereas in the form of embodiment according to FIGS. 1 to 5 they were produced by means of transmitted light.

We claim:

1. Apparatus for three-dimensional inspection of hollow bodies comprising: a conveyor for moving the hollow bodies through an inspection region over a circular path with simultaneous rotation of the hollow bodies about an axis of symmetry which is parallel to the axis of the circular path, an illumination device for illuminating the hollow bodies in the inspection region, a photoelectric transducer for receiving light originating from the illumination device and passing through the hollow bodies which are in the inspection region, and a group of fixed planar mirrors, which are arranged in angular relationship to one another in the path of the light from the hollow bodies in the inspection region and wherein, the illumination device homogeneously illuminates the hollow bodies within the inspection region, the photoelectric transducer is part of a matrix or line-scanning camera having an associated processor and monitor for image processing, and the group has n stationary, planar mirrors arranged between the inspection region and the matrix or line camera, and the n mirrors are angularly disposed and offset in such a way that light is simultaneously detected from the entire inspection region and light emerging from n mutually contiguous segments of the inspection region is simultaneously directed via the n mirrors respectively onto the photoelectric transducer at positions so offset that n partial images of a bottle—one each from one segment of the inspection region—are recorded by said transducer.

2. An apparatus according to claim 1, wherein the illumination device illuminates the hollow bodies within the inspection region with transmitted illumination.

3. An apparatus according to claim 1, wherein the illumination device illuminates the hollow bodies within the inspection region with incident light.

4. An apparatus according to claim 2, wherein the illumination device is a point light source which illuminates the hollow bodies in the inspection region with a fan-shaped beam via a dispersive lens and slit diaphragms.

5. An apparatus according to claim 2, wherein the illumination device produces scattered light with a diffusely transparent plate.

6. An apparatus according to claim 1, wherein the ratio of the speed of rotation of the hollow bodies to the conveyor speed is selected so that each hollow body executes inside the inspection region, altogether one complete revolution about its axis of symmetry and 1/n of a revolution in front of each mirror.

7. An apparatus according to claim 1, wherein the angular separation of the hollow bodies on the circular path of the conveyor is 2/n of the angle subtended by the inspection region.

8. An apparatus according to claim 1, wherein the directions of rotation of the hollow bodies about the axis of symmetry and of the movement of the conveyor are selected so that the speed of rotation of the hollow bodies and the speed of rotation of the conveyor are added in the inspection region.

9. An apparatus according to claim 1, wherein the mirrors are arranged offset in height one behind the other and are so angled with respect to the vertical and to each other that images of the same vertical region of the hollow body are projected onto the photoelectric transducer by the mirrors, and the images from different locations along the circular path are projected onto the transducer in a sequence.

10. An apparatus according to claim 1, wherein the angular positions of all the mirrors are adjustable.

11. An apparatus according to claim 1, wherein a reflecting mirror is arranged in the path of light rays between the group of mirrors and the photoelectric transducer.

* * * * *